United States Patent
Sanderson et al.

Patent Number: 6,093,717
Date of Patent: Jul. 25, 2000

[54] IMIDAZOPYRIDINE THROMBIN INHIBITORS

[75] Inventors: Philip E. Sanderson, Philadelphia; Adel M. Naylor-Olsen, Lansdale, both of Pa.

[73] Assignee: Merck & Co., Inc., Rahway, N.J.

[21] Appl. No.: 09/320,339

[22] Filed: May 26, 1999

Related U.S. Application Data

[60] Provisional application No. 60/086,723, May 26, 1998.

[51] Int. Cl.[7] ............... A61K 31/497; A61K 31/437; A61K 31/4375; C07D 471/04
[52] U.S. Cl. ............... 514/253; 514/300; 544/58.2; 544/120; 544/238; 544/295; 544/357; 544/405; 544/58.6; 546/121
[58] Field of Search ............... 544/405; 514/253

[56] References Cited

U.S. PATENT DOCUMENTS

| | | | |
|---|---|---|---|
| 5,260,307 | 11/1993 | Ackermann et al. | 514/323 |
| 5,405,854 | 4/1995 | Ackermann et al. | 514/315 |
| 5,510,369 | 4/1996 | Lumma et al. | 514/422 |
| 5,550,131 | 8/1996 | Sugihara et al. | 514/255 |
| 5,744,486 | 4/1998 | Sanderson et al. | 514/318 |
| 5,866,573 | 2/1999 | Sanderson et al. | 514/235.8 |

FOREIGN PATENT DOCUMENTS

| | | |
|---|---|---|
| WO 94/25051 | 11/1994 | WIPO. |
| WO 96/11697 | 4/1996 | WIPO. |
| WO 96/31504 | 10/1996 | WIPO. |
| WO 96/32110 | 10/1996 | WIPO. |
| WO 97/01338 | 1/1997 | WIPO. |
| WO 98/42342 | 10/1998 | WIPO. |

*Primary Examiner*—Emily Bernhardt
*Attorney, Agent, or Firm*—Richard S. Parr; Melvin Winokur

[57] ABSTRACT

Compounds of the invention are useful in inhibiting thrombin and associated thrombotic occlusions having the following structure:

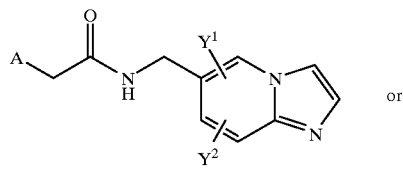

or

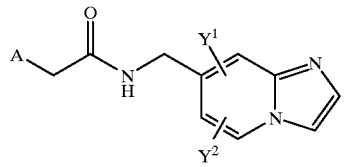

wherein $Y^1$ and $Y^2$ are independently selected from the group consisting of hydrogen, $C_{1-4}$ alkyl, $C_{1-4}$ alkoxy, $C_{3-7}$ cycloalkyl, halogen, and trifluoromethyl; and A is

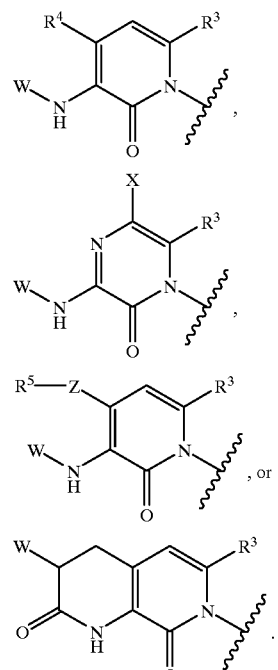

6 Claims, No Drawings

IMIDAZOPYRIDINE THROMBIN INHIBITORS

CROSS-REFERENCE TO RELATED APPLICATIONS

This patent application is a non-provisional patent application claiming priority to U.S. provisional application Ser. No. 60/086,723, filed May 26, 1998.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention, useful as thrombin inhibitors and having therapeutic value in for example, preventing coronary artery disease, have the following structure (formula I or II):

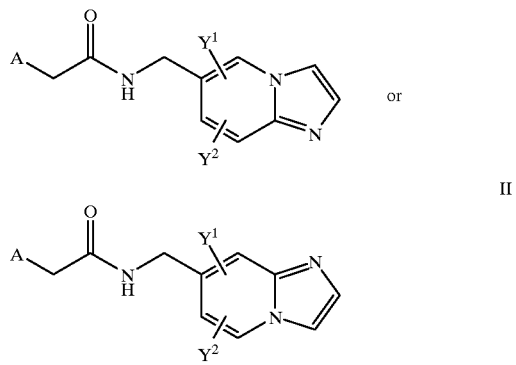

or a pharmaceutically acceptable salt thereof, wherein
$Y^1$ and $Y^2$ are independently selected from the group consisting of
hydrogen,
$C_{1-4}$ alkyl,
$C_{1-4}$ alkoxy,
$C_{3-7}$ cycloalkyl,
halogen, and
trifluoromethyl;
A is

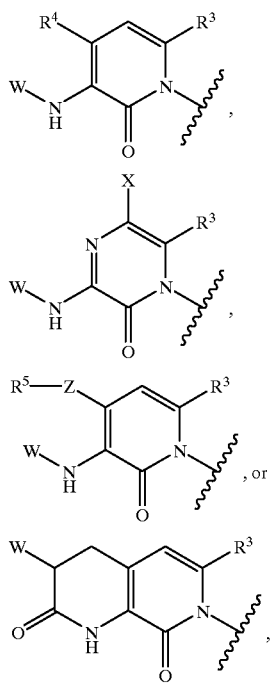

W is
hydrogen,
$R^1$,
$R^1OCO$,
$R^1CO$,
$R^1SO_2$,
$R^1(CH_2)_n NHCO$, or
$(R^1)_2 CH(CH_2)_n NHCO$, wherein n is 0–4;

$R^1$ is $R^2$, $R^2(CH_2)_m C(R^{12})_2$, where m is 0–3, and each $R^{12}$ can be the same or different, $(R^2)(OR^2)CH(CH_2)_p$, where p is 1–4,

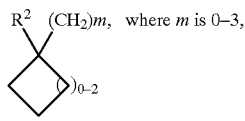

$R^2 C(R^{12})_2 (CH_2)_m$, wherein m is 0–3, and each $R^{12}$ can be the same or different, wherein $(R^{12})_2$ can also form a ring with C represented by $C_{3-7}$ cycloalkyl, $R^2 CH_2 C(R^{12})_2 (CH_2)_q$, wherein q is 0–2, and each $R^{12}$ can be the same or different, wherein $(R^{12})_2$ can also form a ring with C represented by $C_{3-7}$ cycloalkyl, $(R^2)_2 CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S, $R^2 O(CH_2)_p$, wherein p is 1–4, $R^2 CF_2 C(R^{12})_2$, $(R^2 CH_2)(R^2 CH_2)CH$, or $R^2(COOR^6)(CH_2)_r$, where r is 1–4;

$R^2$ and $R^5$ are independently phenyl, unsubstituted or substituted with one or more of $C_{1-4}$ alkyl, $C_{1-4}$ alkoxy, halogen, hydroxy, COOH, $CONH_2$, $CH_2 OH$, $CO_2 R^7$, where $R^7$ is $C_{1-4}$ alkyl, or $SO_2 NH_2$, naphthyl, biphenyl, a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy, $C_{1-7}$ alkyl, unsubstituted or substituted with one or more of hydroxy,

COOH, amino, aryl, $C_{3-7}$ cycloalkyl, $CF_3$, $N(CH_3)_2$,

—$C_{1-3}$alkylaryl, heteroaryl, or heterocycloalkyl, $CF_3$ $C_{3-7}$ cycloalkyl, unsubstituted or substituted with aryl, $C_{7-12}$ bicyclic alkyl, or $C_{10-16}$ tricyclic alkyl;

$R^3$, $R^4$ and $R^6$ are independently selected from the group consisting of hydrogen, $C_{1-4}$ alkyl, $C_{3-7}$ cycloalkyl, or trifluoromethyl;

X is hydrogen, or halogen;

Z is $CH_2$, S, or $SO_2$;

$R^{12}$ is hydrogen, phenyl, unsubstituted or substituted with one or more of $C_{1-4}$ alkyl, $C_{1-4}$ alkoxy, halogen, hydroxy, COOH, $CONH_2$, naphthyl, biphenyl, a 5- to 7-membered mono- or a 9- to 10-membered bicyclic heterocyclic ring which can be saturated or unsaturated, and which contains from one to four heteroatoms selected from the group consisting of N, O and S, $C_{1-4}$ alkyl, unsubstituted or substituted with one or more of hydroxy,

COOH, amino, aryl, heteroaryl, or heterocycloalkyl, $CF_3$ $C_{3-7}$ cycloalkyl, $C_{7-12}$ bicyclic alkyl, or $C_{10-16}$ tricyclic alkyl.

A class of compounds of the invention, or a pharmaceutically acceptable salt thereof, includes those wherein A is

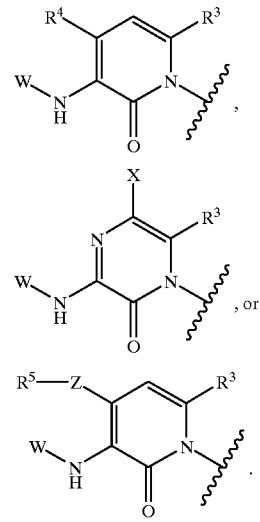

A subclass of compounds of this class, or a pharmaceutically acceptable salt thereof, includes those wherein $Y^1$ and $Y^2$ are hydrogen or $C_{1-4}$ alkyl; W is hydrogen or $R^1$; $R^1$ is $R^2$ or $R^2 SO_2$; $R^2$ and $R^5$ are independently selected from the group consisting of $C_{1-7}$ alkyl unsubstituted or substituted with aryl, $C_{3-7}$ cycloalkyl, or heteroaryl; $R^3$ and $R^4$ are independently selected from the group consisting of hydrogen and $C_{1-4}$ alkyl; and Z is $SO_2$.

In a group of compounds of this subclass, or a pharmaceutically acceptable salt thereof, $Y^1$ and $Y^2$ are hydrogen or methyl; W is hydrogen or

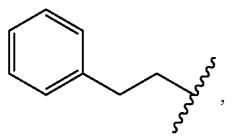

,

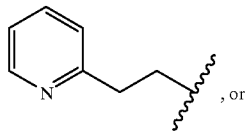

, or

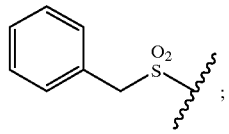

;

$R^5$ is

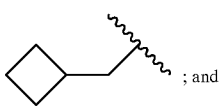

; and $R^3$ and $R^4$ are independently selected from the group consisting of hydrogen and methyl.

Examples of this group are listed below in Table 1. Inhibitory activity of compounds of the invention is represented by "*", indicating Ki greater than or equal to 20 nM, or "**" indicating Ki less than 20 nM. Values are as determined according to the in vitro assay described later in the specification.

TABLE 1

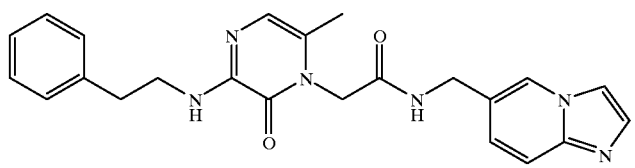

*

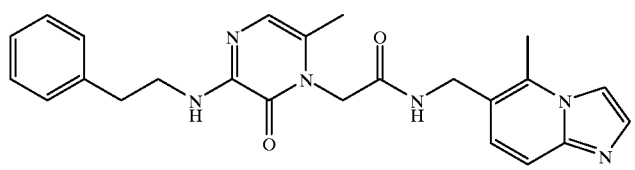

**

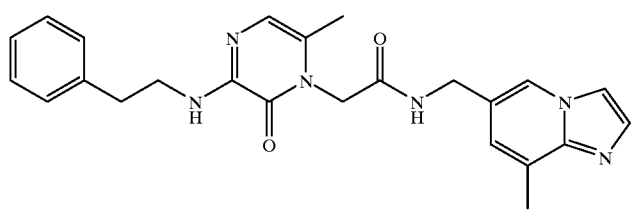

*

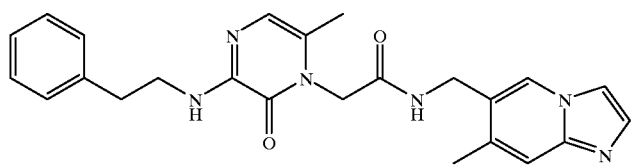

*

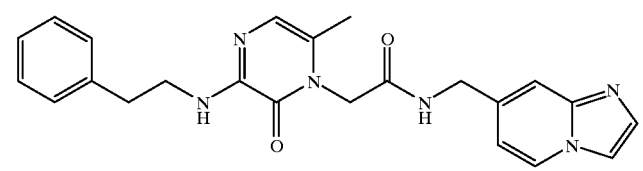

*

TABLE 1-continued

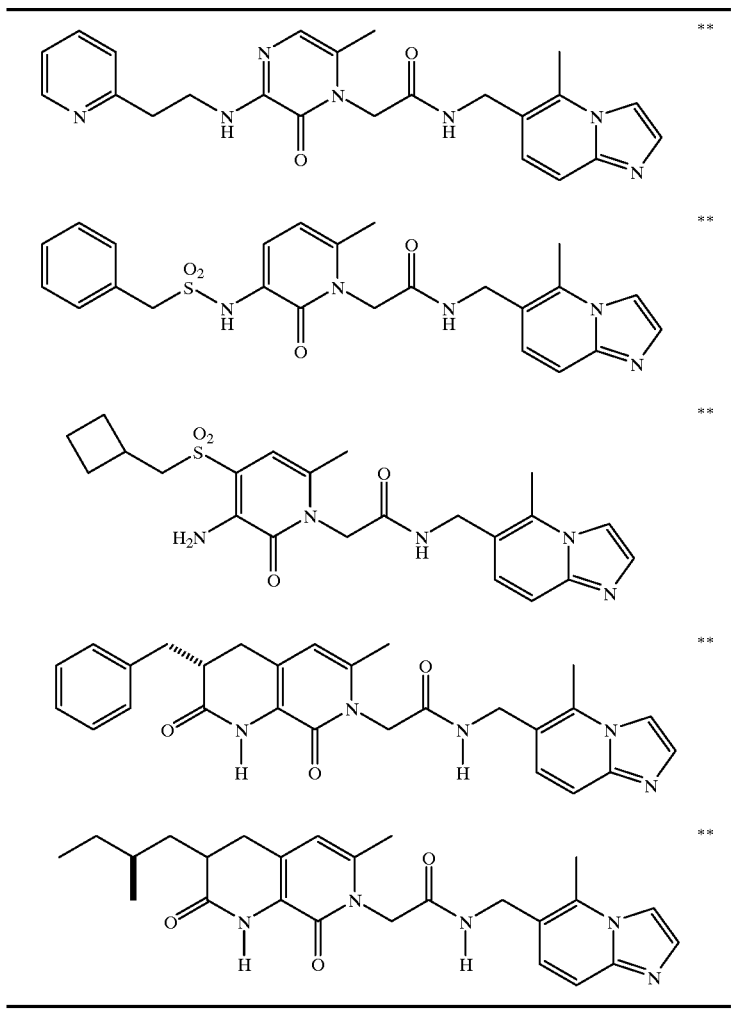

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term "aryl" as used herein except where noted, represents a stable 6- to 10-membered mono- or bicyclic ring system. The aryl ring can be unsubstituted or substituted with one or more of $C_{1-4}$ lower alkyl; hydroxy; alkoxy; halogen; amino. Examples of "aryl" groups include phenyl and naphthyl.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiophenyl, oxazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl. Unsaturated heterocyclic rings may also be referred to hereinafter as "heteroaryl" rings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |

| -continued | |
|---|---|
| HBT(HOBT or HOBt) Designation | 1-hydroxybenzotriazole hydrate Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride Other |
| (BOC)$_2$O (BOC$_2$O) | di-t-butyl dicarbonate |
| n-BU$_4$N + F- | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine Amino Acid |
| Ile | Isoleucine |
| Phe | Phenylalanine |
| Pro | Proline |
| Ala | Alanine |
| Val | Valine |

In Vitro Assay For Determining Proteinase Inhibition

Assays of human α-thrombin and human trypsin were performed by the methods substantially as described in *Thrombosis Research,* Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors (Ki <10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki), which is at least 1000 nM.

Thrombin Inhibitors—Therapeutic Uses Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. he active ingredient can be compressed into pellets or small cylinders nd implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/g patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical uncoated tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including anti-hypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional antiplatelet agents, anticoagulation agents, or thrombolytic agents, depending on a patient's therapeutic needs.

The following synthetic method can be used to prepare the compounds of the present invention. As exemplified by Example 1, the starting aninopyridine is reacted with an α-halo acetaldehyde equivalent such as bromoacetaldehyde using a base such as an acetic acid salt. The bromoacetaldehyde may be generated by acid catalysed hydrolysis from the corresponding acetal, in this case the diethyl acetal.

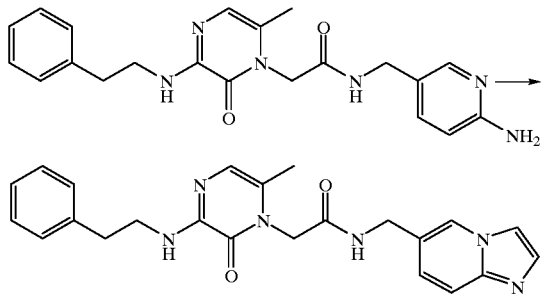

The following examples are illustrative of the invention as contemplated by the inventors and should not be construed as being limits on the scope or spirit of the instant invention. Starting materials are described in the identified patent publications:

- 3-(2-Phenethylamino)-6-methyl-1-(2-amino-5-methylcarboxamidomethylpyridinyl)-pyrazinone (see WO 97/40024);
- 3-(2-Phenethylamino)-6-methyl-1-(2-amino-6-methyl-5-methylcarboxamidomethylpyridinyl)-pyrazinone (see WO 97/40024);
- 3-(2-Phenethylamino)-6-methyl-1-(2-amino-4-methylcarboxamidomethylpyridinyl)-pyrazinone (see WO 97/40024);
- 3-[2-(2-Pyridyl)ethylamino]-6-methyl-1-(2-amino-6-methyl-5-methylcarboxamidomethylpyridinyl)-pyrazinone (see WO 97/40024); and
- 3-Benzylsulfonylamino-6-methyl-1-(2-amino-6-methyl-5-methylcarboxamidomethylpyridinyl)-2-pyridinone (see WO 97/01338).
- 3-(2-Phenethylamino)-6-methyl-1-(2-amino-3-methyl-5-methylenecarboxamidomethylpyridinyl)-pyrazinone (I-1), used in Example 3, is prepared as follows:

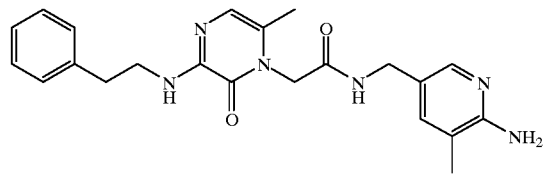

I-1

EDC.HCl (115 mg, 0.60 mmol) was added to a stirred mixture of 3-(2-phenethylamino)-6-methyl-1-carboxymethylpyrazinone (144 mg, 0.50 mmol), 2-amino-5-aminomethyl-3-methylpyridine dihydrochloride (105 mg, 0.50 mmol), HOBT.H$_2$O (81 mg, 0.60 mmol) and N-methylmorpholine (0.275 mL, 2.5 mmol) in dry DMF (4.3 mL). After 4 h the volatiles were evaporated in vacuo and the residue was suspended in dilute sodium carbonate solution and collected by filtration, washing with water, and dried to give the crude free base of the title compound. This material was purified by flash column chromatography on silica (methanol/chloroform gradient, 5–10% methanol) to give I-1 as a white crystalline solid, m.p. >200° C.; $^1$H NMR (DMSO-d$_6$): δ 2.02 (s, 3H, CH$_3$), 2.04 (s, 3H, CH$_3$), 2.85 (t, J=7.4 Hz, 2H, PhCH$_2$), 3.48 (q, J=6.9 Hz, 2H, CH$_2$NH), 4.09 (d, J=5.5 Hz, 2H, CONHCH$_2$), 4.58 (s, 2H, CH$_2$CO), 5.60 (s, 2H, NH$_2$), 6.64 (s, 1H, pyrazinone H-5), 6.80 (br t, J=5.6 Hz, 1H, NH), 7.13 (s, 1H, pyridine H-4), 7.17–7.31 (m, 5H, Ph), 7.69 (s, 1H, pyridine H-6), 8.51 (br t, J=5.6 Hz, 1H, CONH.

3-(2-Phenethylamino)-6-methyl-1-(2-amino-4-methyl-5-methylcarboxamidomethylpyridinyl)-pyrazinone bis-HCl salt (I-1a), used in Example 4, is prepared as follows:

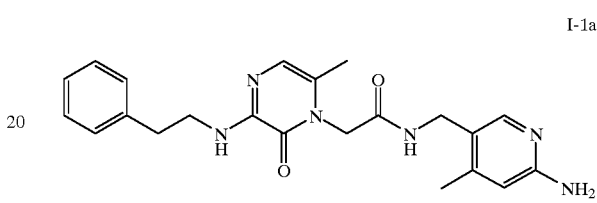

I-1a 3-(2-Phenethylamino)-6-methyl-1-(2-t-butoxycarbonylamino-4-methyl-5-methylcarboxamidomethylpyridinyl)-pyrazinone was prepared from 2-t-butoxycarbonylamino-5-aminomethyl-4-methylpyridine dihydrochloride using the method described for the preparation of I-1, as a colorless solid. This free base (148 mg) was dissolved in ethyl acetate (10 mL) and HCl gas was bubbled through at 0° C. for 15 min. After a further 1.5 h at rt, the volatiles were evaporated to give the title compound as a colorless solid:

$^1$H NMR (CD$_3$OD): d 2.20 (s, 3H, CH$_3$), 2.42 (s, 3H, CH$_3$), 3.01 (t, J=7.4 Hz, 2H, PhCH$_2$), 3.48 (t, J=7.4 Hz, 2H, CH$_2$NH), 4.35 (d, J=5.5 Hz, 2H, CONHCH$_2$), 4.77 (s, 2H, CH$_2$CO), 6.54 (s, 1H, pyrazinone H-5), 6.85 (s, 1H, pyridine H-3), 7.20–7.33 (m, 5H, Ph), 7.72 (s, 1H, pyridine H-6), 8.81 (br t, 1H, CONH).

3-Amino-4-cyclobutylmethylsulfonyl-6-methyl-1-(2-amino-6-methyl-5-methylenecarboxamidomethylpyridinyl)-pyridinone (II-1), used in Example 6, is prepared as follows:

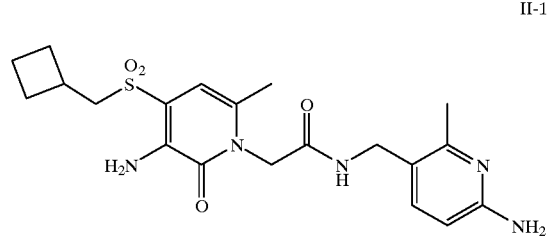

II-1

II-1 was prepared from bromomethylcyclobutane using the procedures for making III-6, Steps A–F, shown below.
$^1$H NMR (d6 DMSO) d 1.76–2.01 (m, 6H), 2.16 (s, 3H), 2.44 (s, 3H), 2.60 (m, 1H), 3.35 (d, J=7.1 Hz, 2H), 4.16 (d, J=5.1 Hz, 2H), 4.67 (s, 2H), 6.10 (br s, 2H), 6.15 (s, 1H), 6.80 (d, J=9.0 Hz, 1H), 7.66 (br s, 2H), 7.76 (d, J=9.0 Hz, 1H), 8.73 (br t, 1H).

3-Amino-4-cyclopropylmethylsulfonyl-6-methyl-1-(2-amino-6-methyl-5-methylenecarboxamidomethylpyridinyl)-2-pyridinone (III-6)

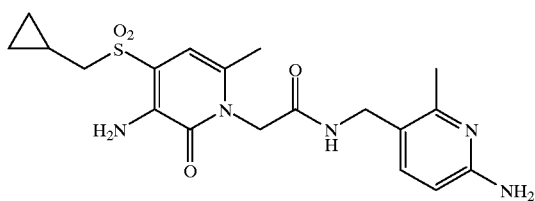

was prepared as follows:

Step A: 2-Cyclopropylmethylthiobenzothiazole (III-1)

A stirred mixture of 2-mercaptobenzothiazole (1.67 g, 10.0 mmol), bromomethylcyclopropane (0.97 mL, 10.0 mmol) and sodium hydrogencarbonate (0.84 g, 10.0 mmol) in absolute ethanol (10 ml) was heated to reflux. After 8 h, the reaction was diluted with ethyl acetate and was washed with water, sodium carbonate solution and brine, dried ($Na_2SO_4$) and evaporated in vacuo to give III-1 as an oil which was used without purification in the next step:

$^1$H NMR (300 Mz, $CDCl_3$) selected signals d 0.39 (m, 2H), 0.65 (m, 2H), 1.26 (m, 1H), 3.32 (d, J=7.3 Hz, 2H).

Step B: 2-Cyclopropylmethylsulfonylbenzothiazole (III-2)

A solution of potassium permanganate (1.90 g, 12.0 mmol) in water (100 mL) was added to a stirred solution of 2-cyclopropylmethylthiobenzothiazole (1.90 g) in acetic acid (150 mL). After 2 h, the dark brown mixture was decolorized with 10% sodium sulfite solution and water (500 mL) was added. The resulting precipitate was collected by filtration, washing with water, and dried at 0.5 mm Hg, to give 111-2 as a white crystalline solid.

$^1$H NMR (300 Mz, $CDCl_3$) selected signals d 0.28 (m, 2H), 0.64 (m, 2H), 1.21 (m, 1H), 3.46 (d, J=7.3 Hz, 2H).

Step C: 4-Cyclopropylmethylsulfonyl-6-methyl-3-nitro-1-(ethyl-methylenecarboxy)-2-pyridinone (III-3)

Sodium borohydride (113 mg, 3.0 mmol) was added in portions to a stirred mixture of 2-cyclopropylmethylsulfonylbenzothiazole (0.38 g, 1.50 mmol) in absolute ethanol (3 mL) with cooling. After 2 h, glacial acetic acid was added dropwise to dissolve the suspension, giving a solution pH 4–5 (moist pH paper) and 4-chloro-6-methyl-3-nitro-1-(ethyl-methylenecarboxy)-2-pyridinone (275 mg, 1.0 mmol) was added. The solid quickly dissolves and then a thick precipitate forms. After 2 h the solids were collected by filtration, washing with ethanol, and dried at 0.5 mm Hg to give III-3 as a bright yellow powder.

$^1$H NMR ($CDCl_3$) d 0.40 (m, 2H), 0.70 (m, 2H), 1.13 (m, 1H), 1.32 (t, J=7.1 Hz, 3H), 2.46 (s, 3H), 3.33 (d, J=7.3 Hz, 2H), 4.28 (q, J=7.1 Hz, 2H), 4.88 (s, 2H), 6.62 (s, 1H)

Step D: 3-Amino-4-cyclopropylmethylsulfonyl-6-methyl-1-(ethylmethylenecarboxy)-2-pyridinone (III-4)

A mixture of 4-cyclopropylmethylsulfonyl-6-methyl-3-nitro-1-(ethyl-methylenecarboxy)-2-pyridinone (365 mg) and 10% palladium on carbon (0.30 g) in ethyl acetate (100 mL) was stirred under an atmosphere of hydrogen (balloon) for 3 h. The reaction mixture was filtered through celite, washing with ethyl acetate, and evaporated in vacuo to give III-4 as a colorless crystalline solid which was used without purification in the next step.

$^1$H NMR ($CDCl_3$) d 0.27 (m, 2H), 0.63 (m, 2H), 1.08 (m, 1H), 1.30 (t, J=7.1 Hz, 3H), 2.23 (d, J=0.9 Hz, 3H), 3.02 (d, J=7.1 Hz, 2H), 4.25 (q, J=7.1 Hz, 2H), 4.80 (s, 2H), 5.88 (br s, 2H), 6.28 (d, J=0.9 Hz, 1H).

Step E: 3-Amino-4-cyclopropylmethylsulfonyl-6-methyl-1-methylenecarboxy-2-pyridinone (III-5)

Lithium hydroxide hydrate (84 mg, 2.0 mmol) was added to a stirred mixture of 3-amino-4-cyclopropylmethylsulfonyl-6-methyl-1-(ethyl-methylenecarboxy)-2-pyridinone (the product from Step D) in 2:2:1 methanol/THF/water (10 mL). After 2 h a thick white precipitate formed. The mixture was acidified with 1 M HCl to give a clear solution which was partitioned between methylene chloride and brine. The brine was re-extracted with methylene chloride and the combined organic layers were dried ($Na_2SO_4$) and evaporated in vacuo to give a crystalline solid. This was heated to reflux as a suspension in methylene chloride (10 mL), cooled and the solids collected by filtration to give III-5 as a colorless crystalline solid.

$^1$H NMR (d6 DMSO) d 0.25 (m, 2H), 0.50 (m, 2H), 0.92 (m, 1H), 2.20 (s, 3H), 3.18 (d, J=7.1 Hz, 2H), 4.73 (s, 2H), 6.16 (br s, 2H), 6.20 (s, 1H).

Step F: 3-Amino-4-cyclopropylmethylsulfonyl-6-methyl-1-(2-amino-6-methyl-5-methylenecarboxamidomethylpyridinyl)-2-pyridinone (III-6)

N-Methylmorpholine (0.187 mL, 1.70 mmol) was added to a stirred mixture of 3-amino-4-cyclopropylmethylsulfonyl-6-methyl-1-methylenecarboxy-2-pyridinone (120 mg, 0.40 mmol), 2-amino-5-aminomethyl-6-methylpyrinine dihydrochloride (84 mg, 0.40 mmol), EDC.HCl (96 mg, 0.50 mmol) and HOBT.H2O (68 mg, 0.50 mmol) in DMF (2 mL). After 16 h, water (20 mL) was added to give a white precipitate and after allowing to stand for 30 min, the solids were collected by filtration, washing with water, ethanol and ethyl acetate and air dried. 9.9 M HCl in absolute ethanol (0.1 mL) was added to a stirred fine suspension of the resulting white solid in absolute ethanol (5 mL) to give a solution. Over 1 h a pale yellow crystalline precipitate formed which was collected by filtration, washing with ethanol and dried at 0.5 mm Hg to give III-6 as a pale peach colored crystalline solid.

$^1$H NMR (d6 DMSO) d 0.25 (m, 2H), 0.50 (m, 2H), 0.91 (m, 1H), 2.17 (s, 3H), 2.44 (s, 3H), 3.17 (d, J=7.1 Hz, 2H), 4.16 (d, J=5.6 Hz, 2H), 4.68 (s, 2H), 6.12 (br s, 2H), 6.18 (d, J=0.7 Hz, 1H), 6.80 (d, J=9.0 Hz, 1H), 7.63 (br s, 2H), 7.76 (d, J=9.0 Hz, 1H), 8.72 (br t, J=5.6 Hz, 1H); Anal. Calc. for C19H25N5O4S.HCl.2H2O: $C_{46.38}$, H 6.15, N 14.24. Found: $C_{46.51}$, H 6.08, N 13.89.

[R]-7-(2-amino-6-methyl-5-methylenecarboxamidomethylenepyridinyl)-3-benzyl-6-methyl-2-oxo-1,2,3,4-tetrahydro-1,7-naphthiridin-[7H]-8-one (IV-11), used in Example 9, is prepared as follows:

(IV-11)

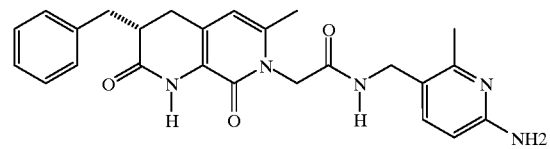

Step A: Ethyl 6-methyl-3-nitropyridone 4-carboxylate

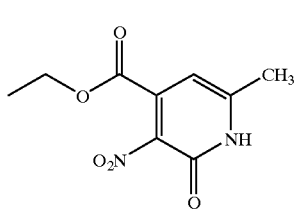

(IV-1)

To a slurry nitroacetamide ammonia salt (70.3 g, 581 mmol) in 400 mL of deionized water was added 100 g (633 mmol, 1.09 equiv.) of ethyl 2,4-dioxovalerate followed by a solution of piperdinium acetate (prepared by adding 36 mL of piperdine to 21 mL of acetic acid in 100 mL of water). The resulting solution was stirred at 40° C. for 16 h then cooled in an ice bath. The precipitated product was filtered and washed with 50 mL of cold water to afford the above pyridone as a yellow solid.

$^1$H NMR (CDCl$_3$) d 6.43 (s, 1H), 4.35 (q, J=7 Hz, 2H), 2.40 (s, 3H), 1.35 (t, J=7 Hz, 3H).

Step B: Ethyl 2-methoxy-6-methyl-3-nitropyridine 4-carboxylate

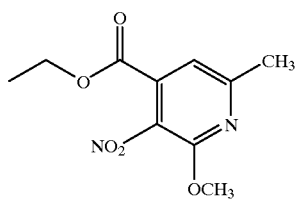

(IV-2)

A solution of the pyridone from step A (6.2 g, 27.4 mmol) in 50 mL of DCM was treated with 4.47 g (30.2 mmol) of solid trimethyloxonium tetrafluoroborate and the mixture was stirred at 40° C. until the reaction was judged to be complete by HPLC (typically 24–72 h). The reaction mixture was concentrated to one-third volume, loaded onto a silica gel column and eluted with 2:3 EtOAc/Hexane to afford the methoxy pyridine as a yellow liquid.

$^1$H NMR (CDCl$_3$) d 7.2 (s, 1H), 4.35 (q, J=7 Hz, 2H), 4.05 (s, 3H), 2.55 (s, 3H), 1.35 (t, J=7 Hz, 3H).

Step C: 4-Hydroxymethyl-2-methoxy-6-methyl-3-nitropyridine

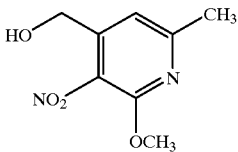

(IV-3)

To a −70° C. solution of ester from step B (5.4 g, 22.5 mmol) in 140 mL of DCM was added 56.2 mL (56.2 mmol) of DIBAL-H (1M in hexane) by dropping funnel. The resulting solution was stirred for 1 h then warmed to room temperature over an additional hour. The reaction mixture was quenched by the careful addition of saturated NaK tartrate. Stirring was continued for 30 min then the solid was filtered and washed with 100 mL of DCM. The filtrate was extracted with 2×50 mL of saturated NaK tartrate then brine (25 mL). The yellow solution was concentrated and chromatographed (2:3 EtOAc/Hexane) to afford the desired alcohol as a yellow solid.

$^1$H NMR (CDCl$_3$) d 7.00 (s, 1H), 4.70 (s, 2H), 4.05 (s, 3H), 2.50 (s, 3H), 2.10 (bs, 1H).

Step D: 4-Formyl-2-methoxy-6-methyl-3-nitropyridine

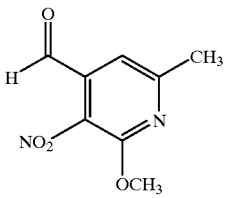

(IV-4)

To a −70° C. solution of oxalyl chloride (2.0 mL, 22 mmol) in 50 mL of DCM was added 3.4 mL (44 mmol) of DMSO in 10 mL of DCM by dropping funnel. After 2 min, the reaction mixture was treated with 3.99 g (20 mmol) of the alcohol from step C in 20 mL of DCM. The solution was stirred for an additional 15 min at −70° C., treated with 14 mL (50 mmol) of Et$_3$N and warmed to ambient temperature over 90 min. The reaction was quenched with 100 mL of water and the two phases were separated. The aqueous phase was extracted with 100 mL of DCM and the combined organic extracts were washed with 50 mL of brine and dried over MgSO$_4$. The yellow solution was concentrated and chromatographed (2:3 EtOAc/Hexane) to afford the aldehyde as a yellow solid.

$^1$H NMR (CDCl$_3$) d 10.05 (s, 1H), 7.10 (s, 1H), 4.70 (s, 2H), 4.05 (s, 3H), 2.60 (s, 3H).

Step E: Methyl-2-benzyl-3-(4-[6-methyl-2-methoxy-3-nitropyridyl])acrylate:

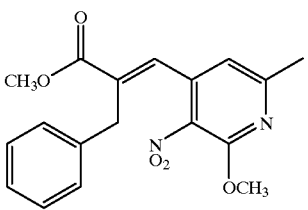

(IV-5)

To a 0° C. solution of 2-benzyl-trimethylphosphonoacetate (1.36 g, 5.0 mmol) in 25 mL of THF was added 145 mg (4.75 mmol) of NaH. The mixture was stirred for 30 min before the dropwise addition of 930 mg (4.75 mmol) of 4-formyl-2-methoxy-3-nitropyridine in 15 mL of THF. The solution was then heated at 50° C. for 3h, cooled and evaporated. The residue was redissolved in 100 mL of EtOAc and quenched to pH=7 with saturated NH$_4$Cl. The organic phase was washed with brine and dried over MgSO$_4$. Column chromatography (2:3 EtOAc/Hexane) afforded the desired olefin as a mixture of E- and Z-isomers.

$^1$H NMR (CDCl$_3$) d 7.60 (s, 1H), 7.40–7.00 (m, 6H), 6.60 (2 singlets, 2H), 4.00 (2 singlets, 6H), 3.75 (2 singlets, 8H), 2.40 (2 singlets, 6H).

Step F: [RS]-3-benzyl-6-methyl-8-methoxy-2-oxo-1,2,3,4-tetrahydro-1,7-naphthiridine:

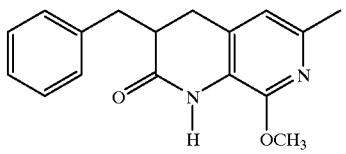
(IV-6)

To a solution of nitro olefin from step E (1.6 g, 4.75 mmol) in 50 mL of EtOAc was added 400 mg of 10% Pd(C). Hydrogen gas was added and the solution was heated at 50° C. for 16. The reaction mixture was filtered through Celite and the filtrate evaporated. Column chromatography (2:3 EtOAc/Hexane) afforded the bicyclic lactam as a white solid.

$^1$H NMR (CDCl$_3$) d 7.45 (bs, 1H), 7.40–7.20 (m, 5H), 6.45 (s, 1H), 3.95 (s, 3H), 3.35 (dd, 1H), 2.80 (m, 2H), 2.60 (m, 2H), 2.40 (s, 3H).

Step G: [RS]-3-benzyl-6-methyl-2-oxo-1,2,3,4-tetrahydro-1,7-naphthiridin-[7H]-8-one:

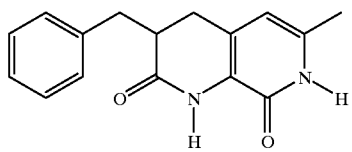
(IV-7)

To a 23° C. solution of methoxypyridine from step F (700 mg, 2.48 mmol) in 25 mL of dichloroethane was added 8.0 mL (8.0 mmol) of BBr$_3$ (1M in DCM). An insoluble gum precipitates within 5 min and the reaction was allowed to stir an additional 90 min before quenching to pH=8 with saturated NaHCO$_3$. The mixture was diluted with 100 mL of EtOAc and 10 mL THF. The aqueous phase was discarded and the organic solution was washed with 10 mL of water then 10 mL of brine. Evaporation of the solvent left a tan colored solid which was used without further purification.

$^1$H NMR (CDCl$_3$) d 8.20 (bs, 1H), 7.40–7.10 (m, 5H), 5.88 (s, 1H), 3.35 (dd, 1H), 2.80–2.50 (m, 4H), 2.25 (s, 3H).

Step H: [RS]-3-benzyl-7-t-butoxycarbonylmethyl-6-methyl-2-oxo-1,2,3,4-tetrahydro-1,7-naphthiridin-[7H]-8-one:

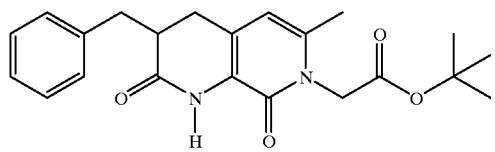
(IV-8)

To a 23° C. solution of pyridone from step G (630 mg, 2.5 mmol) in 20 mL of DMF was added 812 mg (2.5 mmol) of Cs$_2$CO$_3$ and 0.37 mL (2.5 mmol) of tert-butyl bromoacetate. The reaction mixture was allowed to stir for 16 h before removal of the solvent in vacuo. The mixture was diluted with 100 mL of EtOAc and 25 mL water. The aqueous phase was discarded and the organic solution was washed with 20 mL of brine. Evaporation of the solvent and chromatography (1:1 EtOAc/Hexane) of the resulting oil left the alkylated pyridone as a white solid.

$^1$H NMR (CDCl$_3$) d 7.84 (bs, 1H), 7.33–7.17 (m, 5H), 5.87 (s, 1H), 4.79 (q, J=17.2 Hz, 2H), 3.36 (dd, J=4.1,13.5 Hz, 1H), 2.79 (m, 1H), 2.65 (m, 2H), 2.48 (m, 1H), 2.23 (s, 3H), 1.48 (s, 9H).

Step I: [RS]-3-benzyl-7-carboxymethyl-6-methyl-2-oxo-1,2,3,4-tetrahydro-1,7-naphthiridin-[7H]-8-one:

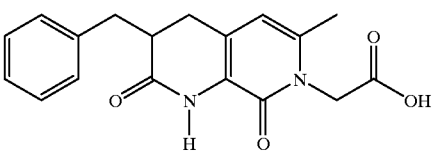
(IV-9)

To a 0° C. solution of ester from step H (310 mg, 0.85 mmol) in 30 mL of DCM was added 8 mL of trifluoroacetic acid. The reaction mixture was allowed to stir to ambient temperature over 5 h before removal of the solvent in vacuo. The resulting solid was azeotroped with benzene, EtOAc then ether. This process yielded the desired carboxylic acid as a white solid.

$^1$H NMR (DMSO-d6) d 8.92 (bs, 1H), 7.35–7.10 (m, 5H), 6.04 (s, 1H), 4.75 (q, J=17.2 Hz, 2H), 3.16 (dd, J=4.2,13.7 Hz, 1H), 2.79 (m, 1H), 2.65–2.40 (m, 3H), 2.1 (s, 3H).

Step J: [RS]-7-(2-t-butoxycarbonylamino-6-methyl-5-methylenecarboxamidomethylenepyridinyl)-3-benzyl-6-methyl-2-oxo-1,2,3,4-tetrahydro-1,7-naphthiridin-[7H]-8-one:

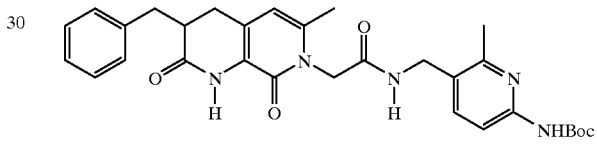
(IV-10)

To a solution of acid from step I (240 mg, 0.90 mmol) and 237 mg (1.0 mmol) of 5-aminomethyl-2-boc-amino-6-methylpyridine in 5 mL of DMF was added 192 mg (1.0 mmol) of EDCI, 135 mg (1.0 mmol) of HOBT and 0.22 mL of N-methylmorpholine. The reaction mixture was allowed to stir for 16 h before removal of the solvent in vacuo. The mixture was diluted with 20 mL of EtOAc and 5 mL water. The aqueous phase was discarded and the organic solution was washed with 3×5 mL of water then 10 mL of brine. Evaporation of the solvent and chromatography (9:1 EtOAc/MeOH) afforded the desired product as a white solid.

$^1$H NMR (CDCl$_3$) d 8.47 (bs, 1H), 7.64 (d, J=9.0 Hz, 1H), 7.43–7.19 (m, 7H), 7.05 (bs, 1H), 5.95 (s, 1H), 4.75 (s, 2H), 4.37 (s, 2H), 3.32 (dd, J=4.1,13.5 Hz, 1H), 2.79–2.0 (m, 4H), 2.45 (s, 3H), 2.35 (s, 3H), 1.58 (s, 9H).

Step K: [R]-7-(2-amino-6-methyl-5-methylenecarboxamidomethylenepyridinyl)-3-benzyl-6-methyl-2-oxo-1,2,3,4-tetrahydro-1,7-naphthiridin-[7H]-8-one:

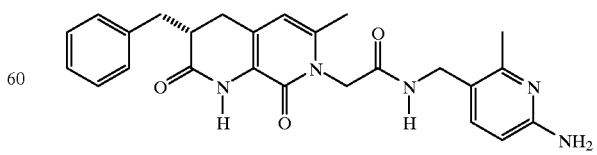
(IV-11)

A solution of bicyclic substrate from step J (410 mg, 0.85 mmol) was dissolved in 12 mL of a 1:1 mixture of DCM and TFA. The reaction mixture was allowed to stir for 3 h before removal of the solvent in vacuo. The resulting solid was azeotroped with benzene, EtOAc then ether. This process yielded the racemate of the desired compound as a white solid. Several 3 mg samples of the free base of this compound were each dissolved in 1 mL of MeOH and the enantiomers were separated on a Chiralcel OD column (250×4.6 mm; A=hexane w/0.1% diethylamine, B=EtOH, A:B=15/85; flow=7 mL/min).

$^1$H NMR (CD$_3$OD) d 7.84 (d, J=9.0 Hz, 1H), 7.40–7.20 (m, 5H), 6.79 (d, J=9.0 Hz, 1H), 6.18 (s, 1H), 4.80 (s, 2H), 4.27 (s, 2H), 3.16 (dd, J=4.1,13.5 Hz, 1H), 2.85–2.44 (m, 4H), 2.0 (s, 3H), 2.38 (s, 3H).

7-(2-amino-6-methyl-5-methylenecarboxamidomethylenepyridinyl)-3-[RS]-(2-[S]-methylbutyl)-6-methyl-2-oxo-1,2,3,4-tetrahydro-1,7-naphthiridin-[7H]-8-one (V-1), used in Example 10, is prepared as follows:

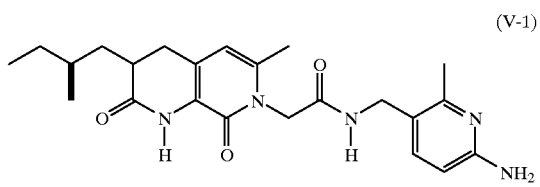

(V-1)

The title compound was prepared by the procedure used to make [RS]-7-(2-amino-6-methyl-5-methylenecarboxamidomethylenepyridinyl)-3-5 benzyl-6-methyl-2-oxo-1,2,3,4-tetrahydro-1,7-naphthiridin-[7H]-8-one: MS (FAB) 426.3 (M+1)$^+$.

EXAMPLE 1

3-(2-Phenethylamino)-6-methyl-1-(5-methylenecarboxamidomethylene-imidazo-[1,2-a]pyridinyl)-pyrazinone dihydrochloride

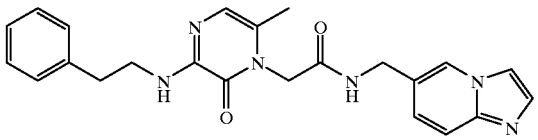

A stirred mixture of bromoacetaldehyde diethyl acetal (0.76 mL, 5.1 mmol) in a solution of cHCl (0.1 mL, 1.2 mmol) in water (4 mL) was heated to reflux for 0.5 h. The resulting single phase solution was cooled, and potassium acetate (0.736 g, 7.5 mmol) was added. An aliquot of this solution (0.20 mL) was added to a stirred thick slurry of 3-(2-phenethyleneamino )-6-methyl-1-(2-amino-5-methylenecarboxamidomethylenepyridinyl)-pyrazinone (see WO 97/40024) (46 mg, 0.10 mmol) and potassium acetate (20mg, 0.20 mmol) in water (0.2 mL). DMF (0.4 mL) was added to give a milky suspension. After 16 h the resulting mixture was acidified with sufficient 1M HCl to give a solution which was diluted with water (20 mL) and washed with methylene chloride. The aqueous layer was neutralized with saturated sodium hydrogen carbonate solution to give a thick precipitate. THF (20 mL) was added, the aqueous layer was saturated with sodium chloride and the product was extracted into the organic layer, which was then dried (Na$_2$SO$_4$) and evaporated to give the free base of the title compound as a colorless solid. The free base was suspended in ethanol (2 mL) and 9.9 Methanolic HCl (4 drops) was added to give a solution which was evaporated in vacuo. Crystallization was induced in 1:1 ethanol/ethyl acetate and the crystalline product was heated to reflux in ethanol (1 mL) for 1 min, cooled and collected by filtration, washing with cold ethanol and diethyl ether to give the title compound as a colorless powder, m.p. >220° C.:

$^1$H NMR (d$_6$ DMSO): δ 2.12 (s, 3H), 2.90 (t, J=7.6 Hz, 2H), 3.62 (br s, 2H, partially obscured), 4.45 (d, J=5.9 Hz, 2H), 4.69 (s, 2H), 6.69 (s, 1H), 7.19– 7.30 (m, 5H), 7.86 (d, J=9.3 Hz, 1H), 7.98 (d, J=9.3 Hz, 1H), 8.21 (d, J=1.9 Hz, 1H), 8.38 (d, J=1.9 Hz, 1H), 8.82 (s, 1H), 9.07 (br t, J=5.9 Hz, 1H); MS (FAB) 417 (M+1)$^+$.

EXAMPLE 2

3-(2-Phenethyleneamino)-6-methyl-1-(4-methyl-5-methylenecarboxamidomethyleneimidazo[1,2-a]pyridinyl)-pyrazinone dihydrochloride

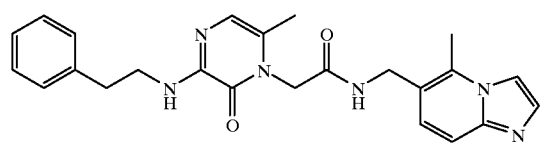

The title compound was prepared from 3-(2-phenethyleneamino)-6-methyl-1-(2-amino-6-methyl-5-methylenecarboxamidomethylenepyridinyl)-pyrazinone (see WO 97/40024) using the procedure of Example 1 as a colorless powder, m.p. >220° C.:

MS (FAB) 431 (M+1)$^+$.

EXAMPLE 3

3-(2-Phenethyleneamino)-6-methyl-1-(7-methyl-5-methylenecarboxamidomethyleneimidazo[1,2-a]pyridinyl)-pyrazinone dihydrochloride

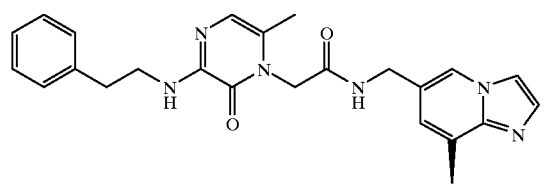

The title compound was prepared from 3-(2-phenethyleneamino)-6-methyl-1-(2-amino-3-methyl-5-methylenecarboxamidomethylenepyridinyl)-pyrazinone (I-1) using the procedure of Example 1, m.p. >200° C.:

MS (FAB) 431 (M+1)$^+$.

EXAMPLE 4

3-(2-Phenethylamino)-6-methyl-1-(6-methyl-5-methylenecarboxamidomethyleneimidazo[1,2-a]pyridinyl)-pyrazinone dihydrochloride

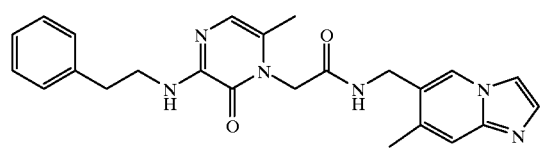

The title compound was prepared from 3-(2-phenethyleneamino)-6-methyl-1-(2-amino-4-methyl-5-methylenecarboxamidomethylenepyridinyl)-pyrazinone see WO 97/40024) using the procedure of Example 1, m.p. 184–186° C.:

MS (FAB) 431 (M+1)⁺.

EXAMPLE 5
3-(2-Phenethyleneamino)-6-methyl-1-(6-methylenecarboxamidomethylene-imidazo[1,2-a]pyridinyl)-pyrazinone

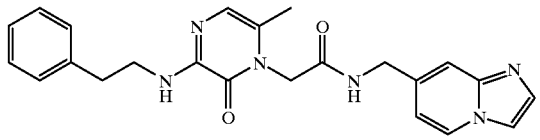

The title compound was prepared as the free base from 3-(2-phenethyleneamino)-6-methyl-1-(2-amino-4-methylenecarbox-amidomethylenepyridinyl)-pyrazinone (see WO 97/40024) using the procedure of Example 1, m.p. >200° C.:

MS (FAB) 417 (M+1)⁺.

EXAMPLE 6
3-Amino-4-cyclobutylmethylenesulfonyl-6-methyl-1-(4-methyl-5-methylenecarboxamidomethyleneimidazo[1,2-a]pyridinyl)-pyridinone hydrochloride

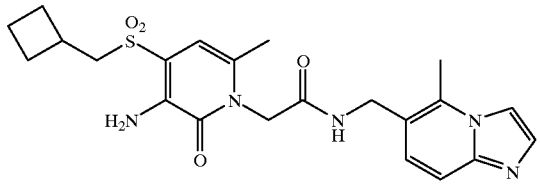

The title compound was prepared from 3-amino-4-cyclobutylmethylenesulfonyl-6-methyl-1-(2-amino-6-methyl-5-methylenecarboxamidomethylenepyridinyl)-pyridinone (11–1) using the procedure of Example 1, m.p. >200° C.:

MS (FAB) 458 (M+1)⁺.

EXAMPLE 7
3-[2-(2-Pyridyl)ethyleneamino]-6-methyl-1-(4-methyl-5-methylenecarboxamidomethyleneimidazo[1,2-a]pyridinyl)-pyrazinone

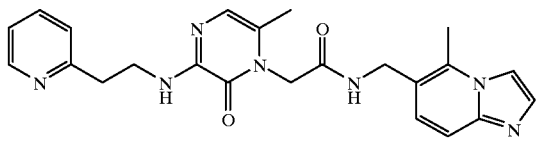

The title compound was prepared as the free base from 3-[2-(2-Pyridyl)ethyleneamino]-6-methyl-1-(2-amino-6-methyl-5-methylenecarboxamidomethylenepyridinyl)-pyrazinone (see WO 97/40024) using the procedure of Example 1, m.p. >200° C.:

MS (FAB) 432 (M+1)⁺.

EXAMPLE 8
3-(2-Phenethyleneamino)-6-methyl-1-(4-methyl-5-methylenecarboxamidomethyleneimidazo[1,2-a]pyridinyl)-pyrazinone hydrochloride

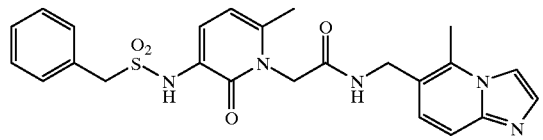

The title compound was prepared from 3-benzylsulfonylamino-6-methyl-1-(2-amino-6-methyl-5-methylenecarboxamidomethylenepyridinyl)-2-pyridinone (see WO 97/01338) using the procedure of Example 1, m.p. 175–181° C.:

MS (FAB) 480 (M+1)⁺.

EXAMPLE 9
[R]-7-(4-methyl-5-methylenecarboxamidomethyleneimidazo[1,2-a]pyridinyl)-3-benzyl-6-methyl-2-oxo-1,2,3,4-tetrahydro-1,7-naphthiridin-[7H]-8-one

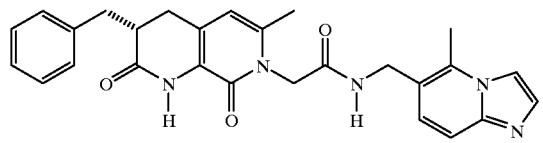

The title compound was prepared from [R]-7-(2-amino-6-methyl-5-methylenecarboxamidomethylenepyridinyl)-3-benzyl-6-methyl-2-oxo-1,2,3,4-tetrahydro-1,7-naphthiridin-[7H]-8-one (IV-11) using the procedure of Example 1:

MS (FAB) 470.2 (M+1)⁺.

EXAMPLE 10
7-(4-methyl-5-methylenecarboxamidomethyleneimidazo[1,2-a]pyridinyl)-3-[RS]-(2-[S]-methylbutyl)-6-methyl-2-oxo-1,2,3,4-tetrahydro-1,7-naphthiridin-[7H]-8-one

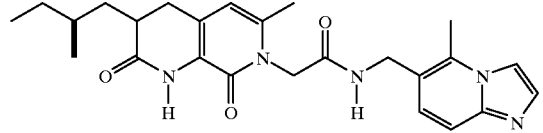

The title compound was prepared from 7-(2-amino-6-methyl-5-methylenecarboxamidomethylenepyridinyl)-3-[RS]-(2-[S]-methylbutyl)-6-methyl-2-oxo-1,2,3,4-tetrahydro-1,7-naphthiridin-[7H]-8-one (V-1) using the procedure of Example 1:

MS (FAB) 450.3 (M+1)⁺.

EXAMPLE 11
Tablet Preparation

Tablets containing 25.0, 50.0, and 100.0 mg., respectively, of the following active compounds are prepared as illustrated below (compositions A-I). Active I is 3-Amino-4-cyclobutylmethylene-sulfonyl-6-methyl-1-(4-methyl-5-methylenecarboxamido-methyleneimidazo[1,2-a]pyridinyl)-pyrazinone hydrochloride; Active II is 3-[2-(2-Pyridyl)ethyleneamino]-6-methyl-1-(4-methyl-5-methylenecarboxamidomethyleneimidazo[1,2-a]pyridinyl)-pyrazinone; Active III is 3-(2-Phenethyleneamino)-6-methyl-1-(4-methyl-5-methylenecarboxamidomethyleneimidazo[1,2-a]pyridinyl)-pyrazinone hydrochloride; and Active TV is 3-(2-Phenethyleneamino)-6-methyl-1-(4-methyl-5- methylenecarboxamidomethyleneimidazo[1,2-a]pyridinyl)-pyrazinone dihydrochloride

TABLE FOR DOSES CONTAINING FROM 25–100MG OF THE ACTIVE COMPOUND

| Component | Amount-mg | | | | | | | | |
|---|---|---|---|---|---|---|---|---|---|
| | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 12

Tablet Preparation

Exemplary compositions of 3-(2-Phenethyleneamino)-6-methyl-1-(4-methyl-5-methylenecarboxamidomethyleneimidazo[1,2-a]pyridinyl)-pyrazinone dihydrochloride tablets are shown below:

| Component | 0.25 mg | 2 mg | 10 mg | 50 mg |
|---|---|---|---|---|
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet preparation via direct compression

Active IV, mannitol and microcrystalline cellulose were sieved through mesh screens of specified size (generally 250 to 750 µm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet preparation via dry granulation

Alternatively, a dry powder blend is compacted under modest forces and remilled to afford granules of specified particle size. The granules are then mixed with magnesium stearate and tabletted as stated above.

EXAMPLE 13

Intravenous Formulations

Intravenous formulations of 3-(2-Phenethyleneamino)-6-methyl-1-(4-methyl-5-methylenecarboxamidomethyleneimidazo[1,2-a]pyridinyl)-pyrazinone dihydrochloride were prepared according to general intravenous formulation procedures.

| Component | Estimated range |
|---|---|
| Active IV | 0.12–0.61 mg |
| D-glucuronic acid* | 0.5–5 mg |
| Mannitol NF | 50–53 mg |
| Water for injection | q.s. 1.0 mL |

1N sodium hydroxide is used to achieve a solution pH in the range of between 3.9–4.1.

Exemplary compositions A-C are as follows:

| Component | A | B | C |
|---|---|---|---|
| Active IV | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base; 0.25 mg free base; *0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound having the formula:

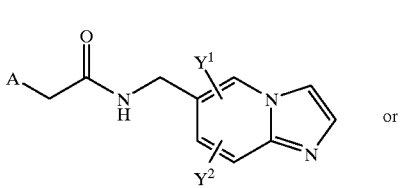

I

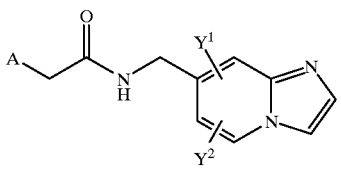

II or a pharmaceutically acceptable salt thereof, wherein
$Y^1$ and $Y^2$ are independently selected from the group consisting of
hydrogen,
$C_{1-4}$ alkyl, $C_{1-4}$ alkoxy,
$C_{3-7}$ cycloalkyl,
halogen, and
trifluoromethyl;

A is

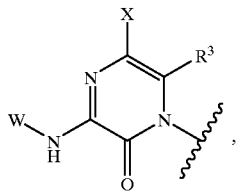,

W is
hydrogen,
$R^1$,
$R^1OCO$,
$R^1CO$,
$R^1SO_2$,
$R^1(CH_2)_nNHCO$, or
$(R^1)_2CH(CH_2)_nNHCO$,
wherein n is 0–4;

$R^1$ is
$R^2$,
$R^2(CH_2)_mC(R^{12})_2$, where m is 0–3, and each $R^{12}$ can be the same or different,
$(R^2)(OR^2)CH(CH_2)_p$, where p is 1–4,

$R^2C(R^{12})_2(CH_2)_m$, wherein m is 0–3, and each $R^{12}$ can be the same or different, wherein $(R^{12})_2$ can also form a ring with C represented by $C_{3-7}$ cycloalkyl,
$R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl,
$(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, or $C_{10-16}$ tricyclic alkyl,
$R^2O(CH_2)_p$, wherein p is 1–4,
$R^2CF_2C(R^{12})_2$,
$(R^2CH_2)(R^2CH_2)CH$, or
$R^2(COOR^6)(CH_2)_r$, where r is 1–4;

$R^2$ is
phenyl, unsubstituted or substituted with one or more of $C_{1-4}$ alkyl, $C_{1-4}$ alkoxy, halogen, hydroxy, COOH, $CONH_2$, $CH_2OH$, $CO_2R^7$, where $R^7$ is $C_{1-4}$ alkyl, or $SO_2NH_2$,
naphthyl,
biphenyl,
$C_{1-7}$ alkyl, unsubstituted or substituted with one or more of hydroxy,
COOH,
amino,
phenyl,
naphthyl,
$C_{3-7}$ cycloalkyl,
$CF_3$,
$N(CH_3)_2$,
—$C_{1-3}$alkylphenyl,
—$C_{1-3}$alkylnaphthyl, or
pyridyl
$CF_3$,
$C_{3-7}$ cycloalkyl, unsubstituted or substituted with phenyl or naphthyl,
$C_{7-12}$ bicyclic alkyl, or
$C_{10-16}$ tricyclic alkyl;

$R^3$, $R^4$ and $R^6$ are independently selected from the group consisting of
hydrogen,
$C_{1-4}$ alkyl,
$C_{3-7}$ cycloalkyl, or
trifluoromethyl;

X is
hydrogen, or
halogen;

Z is $CH_2$, S, or $SO_2$;

$R^{12}$ is
hydrogen,
phenyl, unsubstituted or substituted with one or more of $C_{1-4}$ alkyl, $C_{1-4}$ alkoxy, halogen, hydroxy, COOH, $CONH_2$,
naphthyl,
biphenyl,
$C_{1-4}$ alkyl, unsubstituted or substituted with one or more of hydroxy,
COOH,
amino,
phenyl,
naphthyl, or
$CF_3$,
$C_{3-7}$ cycloalkyl,
$C_{7-12}$ bicyclic alkyl, or
$C_{10-16}$ tricyclic alkyl.

2. A compound of claim 1, or a pharmaceutically acceptable salt thereof, wherein $Y^1$ and $Y^2$ are hydrogen or $C_{1-4}$ alkyl; W is hydrogen or $R^1$; $R^1$ is $R^2$ or $R^2SO_2$; $R^2$ is selected from the group consisting of $C_{1-7}$ alkyl unsubstituted or substituted with phenyl, naphthyl, $C_{3-7}$ cycloalkyl, or; $R^3$ and $R^4$ are independently selected from the group consisting of hydrogen and $C_{1-4}$ alkyl; and Z is $SO_2$.

3. A compound of claim 2, or a pharmaceutically acceptable salt thereof, wherein $Y^1$ and $Y^2$ are hydrogen or methyl; W is hydrogen or

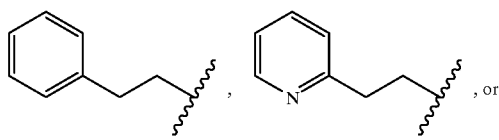, or

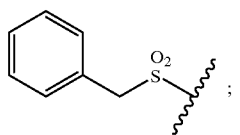;

R⁵ is

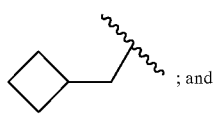 ; and

R³ and R⁴ are independently selected from the group consisting of hydrogen and methyl.

4. A compound of claim 3, or a pharmaceutically acceptable salt thereof, selected from the group consisting of

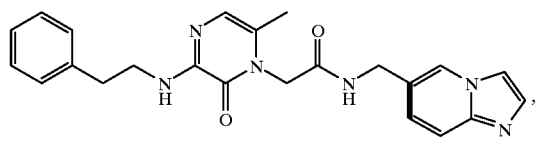

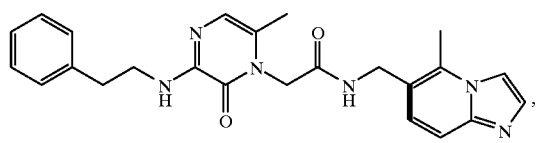

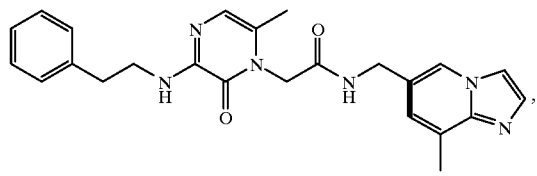

-continued

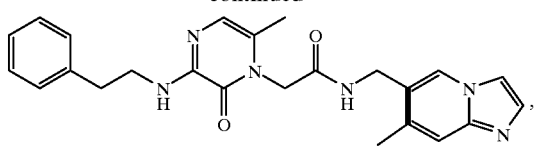

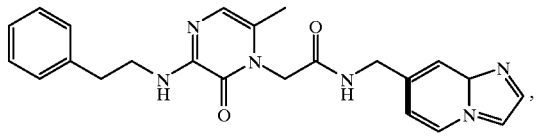

and

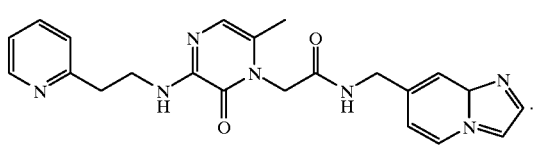

5. A pharmaceutical composition comprising a therapeutically effective amount of a compound of claim 1.

6. A method for inhibiting thrombus formation in blood comprising adding to the blood an effective amount of a composition of claim 5.

* * * * *